US012678598B2

(12) United States Patent
Scherich et al.

(10) Patent No.:  US 12,678,598 B2
(45) Date of Patent:  Jul. 14, 2026

(54) VASCULAR ACCESS DEVICE TO REDUCE BUCKLING OF A PROBE

(71) Applicant: Becton, Dickinson and Company, Franklin Lakes, NJ (US)

(72) Inventors: Megan Scherich, Salt Lake City, UT (US); Yiping Ma, Layton, UT (US); Curtis H. Blanchard, Riverton, UT (US); John Lackey, West Valley City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1051 days.

(21) Appl. No.: 17/852,516

(22) Filed: Jun. 29, 2022

(65) Prior Publication Data

US 2023/0001157 A1      Jan. 5, 2023

Related U.S. Application Data

(60) Provisional application No. 63/218,087, filed on Jul. 2, 2021.

(51) Int. Cl.
  *A61M 25/06*      (2006.01)
  *A61B 5/15*      (2006.01)
  (Continued)

(52) U.S. Cl.
  CPC ... *A61M 25/0606* (2013.01); *A61B 5/150992* (2013.01); *A61M 25/0097* (2013.01); *A61M 25/0113* (2013.01); *A61M 25/09* (2013.01)

(58) Field of Classification Search
  CPC .......... A61M 25/0043; A61M 25/0606; A61M 25/0097; A61M 25/01; A61M 25/0113;
  (Continued)

(56) References Cited

U.S. PATENT DOCUMENTS 11,406,795 B2    8/2022  Burkholz et al.
12,246,149 B2    3/2025  Horst et al.
      (Continued)

FOREIGN PATENT DOCUMENTS

WO      2020014149 A1      1/2020
WO      2020210488 A1    10/2020
WO      2021194761 A1      9/2021

OTHER PUBLICATIONS

U.S. Appl. No. 17/701,124 entitled "Vascular Access Device to Reduce Buckling Of an Instrument".

*Primary Examiner* — Bhisma Mehta
*Assistant Examiner* — Marissa Taylor
(74) *Attorney, Agent, or Firm* — The Webb Law Firm

(57)      ABSTRACT

A vascular access device may include a housing, which may include a distal end, a proximal end, and a slot. An advancement element may extend through the slot and may be configured to move linearly along the slot between a retracted position and an advanced position. In response to movement of the advancement element from the retracted position to the advanced position, a probe of the vascular access device may be advanced beyond the distal end. The vascular access device may include one or more features to reduce buckling of the probe and limit displacement of the probe. For example, the vascular access device may include a protrusion fixed within the housing distal to the advancement element. As another example, the vascular access device may include a distally-extending arm and/or a recess configured to receive the distally extending arm.

8 Claims, 15 Drawing Sheets

(51) Int. Cl.
    *A61M 25/00*      (2006.01)
    *A61M 25/01*      (2006.01)
    *A61M 25/09*      (2006.01)

(58) Field of Classification Search
    CPC ............ A61M 25/09; A61M 25/09041; A61M
                 2025/0019; A61B 5/15003; A61B
          5/150221; A61B 5/150992; A61B 5/153;
                               A61B 5/154
    See application file for complete search history.

(56)                    References Cited

U.S. PATENT DOCUMENTS

| | | | |
|---|---|---|---|
| 2011/0282285 A1 | 11/2011 | Blanchard et al. | |
| 2014/0094774 A1* | 4/2014 | Blanchard ......... | A61M 25/0105 |
| | | | 604/164.08 |
| 2016/0220790 A1 | 8/2016 | Borowicz | |
| 2020/0001051 A1 | 1/2020 | Huang et al. | |
| 2020/0016374 A1* | 1/2020 | Burkholz .............. | A61M 25/09 |
| 2020/0170559 A1* | 6/2020 | Burkholz ......... | A61B 5/150992 |
| 2020/0187967 A1* | 6/2020 | Palushi ............. | A61M 25/1018 |
| 2020/0246590 A1 | 8/2020 | Devgon et al. | |
| 2022/0305236 A1 | 9/2022 | Harding et al. | |

\* cited by examiner

VASCULAR ACCESS DEVICE TO REDUCE BUCKLING OF A PROBE

CROSS-REFERENCE TO RELATED APPLICATION

The present application claims priority to U.S. Provisional Application Ser. No. 63/218,087, entitled "Vascular Access Device to Reduce Buckling of a Probe", filed Jul. 2, 2021, the entire disclosure of which is hereby incorporated by reference in its entirety.

BACKGROUND OF THE INVENTION

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter device includes a catheter that is over-the-needle. As its name implies, the catheter that is over-the-needle may be mounted over an introducer needle having a sharp distal tip. A catheter assembly may include a catheter adapter, the catheter extending distally from the catheter adapter, and the introducer needle extending through the catheter. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal or fluid infusion.

Infusion and blood withdrawal using the catheter may be difficult for several reasons, particularly when an indwelling time of the catheter increase. A fibrin sheath or thrombus may form on an internal surface of the catheter assembly, an external surface of the catheter assembly, or within the vasculature near the distal tip of the catheter. The fibrin sheath or thrombus may block or narrow a fluid pathway through the catheter, which may impair infusion and/or collection of a high-quality blood sample.

The subject matter claimed herein is not limited to embodiments that solve any disadvantages or that operate only in environments such as those described above. Rather, this background is only provided to illustrate one example technology area where some implementations described herein may be practiced.

SUMMARY OF THE INVENTION

The present disclosure relates generally to vascular access devices and related systems and methods. In some embodiments, a vascular access device may include a housing, which may include a proximal end, a distal end, and a slot between the proximal end and the distal end. In some embodiments, the vascular access device may include a protrusion fixed within the housing distal to the advancement element. In some embodiments, the vascular access device may include an advancement element, which may extend through the slot and may be configured to move linearly along the slot between a retracted position and an advanced position. In some embodiments, a distal end of the advancement element may include a recess configured to receive the protrusion when the advancement element is in the advanced position.

In some embodiments, a probe may include a first end and a second end. In some embodiments, the probe may be disposed between the protrusion and an inner surface of the housing. In some embodiments, in response to movement of the advancement element from the retracted position to the advanced position, the second end of the probe may be advanced beyond the distal end of the housing.

In some embodiments, an inner surface of the housing may include a groove disposed within the housing between the proximal end of the housing and the distal end of the housing. In some embodiments, the probe may be configured to move within the groove in response to the advancement element moving linearly along the slot between the retracted position and the advanced position. In some embodiments, the groove may be linear.

In some embodiments, the advancement element may include an arc-shaped channel. In some embodiments, the probe may extend through the arc-shaped channel. In some embodiments, the first end of the probe may be fixed. In some embodiments, in response to movement of the advancement element a first distance, the second end of the probe may be configured to advance distally a second distance. In some embodiments, the second distance may be at least twice the first distance. In some embodiments, the groove may be a first groove, and the inner surface of the housing may include a second groove between the proximal end of the housing and the distal end of the housing and generally parallel to the first groove. In some embodiments, the probe may extend through the second groove.

In some embodiments, the advancement element may include a distally-extending arm. In some embodiments, the probe may be disposed between the distally-extending arm and the inner surface of the housing. In some embodiments, the housing may include a slot configured to receive the distally-extending arm when the advancement element is in the advanced position. In some embodiments, the groove may be disposed within the housing between the proximal end of the housing and the distal end of the housing, and the probe may be configured to move within the groove in response to the advancement element moving linearly along the slot between the retracted position and the advanced position.

In some embodiments, the vascular access device may include a post, which may be coupled to an inner surface of the housing. In some embodiments, the vascular access device may include a motion restrictor rotatably mounted on the post and extending over the groove. In some embodiments, in response to movement of the advancement element from the retracted position to the advanced position, the motion restrictor may be configured to rotate on the post. In some embodiments, the advancement element may include a cutout portion configured to allow the advancement element to move distally past the post and the motion restrictor.

In some embodiments, the vascular access device may include a first probe enclosure and a second probe enclosure. In some embodiments, the first probe enclosure may include a first serpentine slot, and the second probe enclosure may include a second serpentine slot. In some embodiments, the vascular access device may include a first flexible arm extending outwardly from the advancement element and/or through the first probe enclosure. In some embodiments, the probe may extend through a portion of the first flexible arm. In some embodiments, the vascular access device may include a second flexible arm extending outwardly from the advancement element and/or through the second probe enclosure. In some embodiments, the probe may extend through a portion of the second flexible arm. In some embodiments, the probe may include a guidewire.

In some embodiments, the vascular access device may include a first rotatable probe enclosure and/or a second rotatable probe enclosure configured to rotate with respect to the housing. In some embodiments, the first rotatable probe enclosure may include a first helical slot. In some embodiments, the second rotatable probe enclosure may include a second helical slot.

In some embodiments, the probe may extend through the first helical slot and the second helical slot. In some embodiments, in response to movement of the advancement element along the slot, the first rotatable probe enclosure and the second rotatable probe enclosure may be configured to rotate. In some embodiments, the first rotatable probe enclosure and the second rotatable probe enclosure may be tubular.

In some embodiments, another vascular access instrument advancement device may include an advancement element and an extension tube extending through the advancement element. In some embodiments, the extension tube may be a first lumen and a second lumen. In some embodiments, a blood collection pathway may extend through the first lumen.

In some embodiments, the other vascular access device may include a wedge disposed within the advancement element and the second lumen of the extension tube. In some embodiments, the other vascular access device may include a pair of opposing pinch members configured to pinch the extension tube. In some embodiments, the pair of opposing pinch members may be disposed within the advancement element and configured to move along the extension tube with the advancement element.

In some embodiments, the other vascular access device may include the probe extending distally from the wedge and/or disposed within the second lumen. In some embodiments, in response to moving the advancement element distally along the extension tube from a retracted position to an advanced position, the pair of opposing pinch members may push the wedge distally and the probe is advanced distally. In some embodiments, the other vascular access device may include one or more supports disposed within the second lumen distal to the wedge and configured to contact and support the probe.

In some embodiments, in response to movement of the advancement element from the retracted position to the advanced position, the advancement element may be configured to push the supports distally. In some embodiments, the other vascular access device may include a tether, which may be coupled to the advancement element and at least one of the supports. In some embodiments, in response to movement of the advancement element from the advanced position to the retracted position, the tether may be configured to pull the at least one of the supports proximally.

In some embodiments, the supports may include a first protrusion and a second protrusion opposite the first protrusion. In some embodiments, the first protrusion and/or the second protrusion may include a dome shape. In some embodiments, the supports may include a third protrusion and a fourth protrusion opposite the third protrusion. In some embodiments, the third protrusion and/or the fourth protrusion may each include the dome shape.

It is to be understood that both the foregoing general description and the following detailed description are examples and explanatory and are not restrictive of the invention, as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE DRAWINGS

Example embodiments will be described and explained with additional specificity and detail through the use of the accompanying drawings in which.

5

Figure 4A:
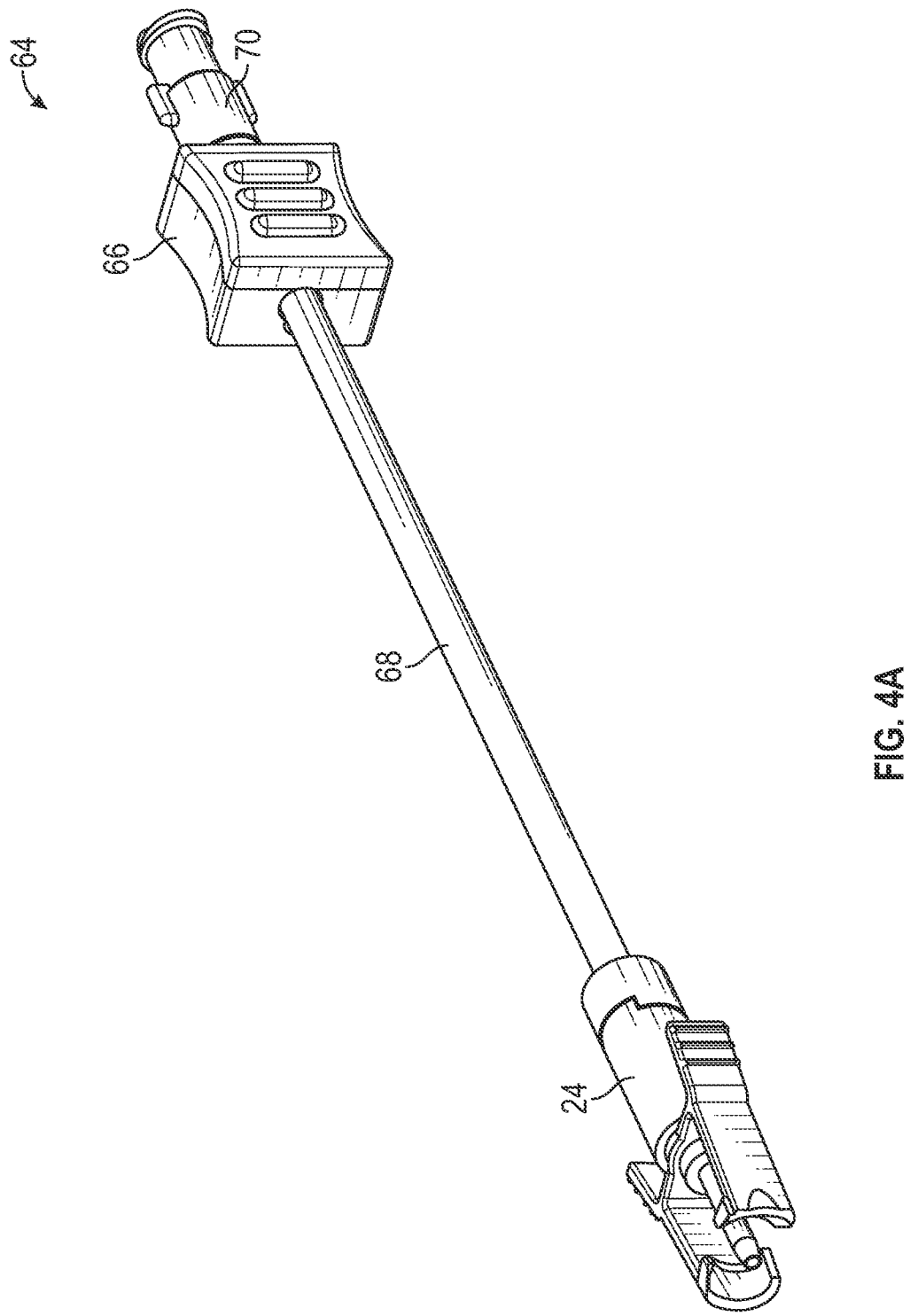
FIG. 4A is an upper perspective view of another example vascular access device, according to some embodiments.
Figure 4B:
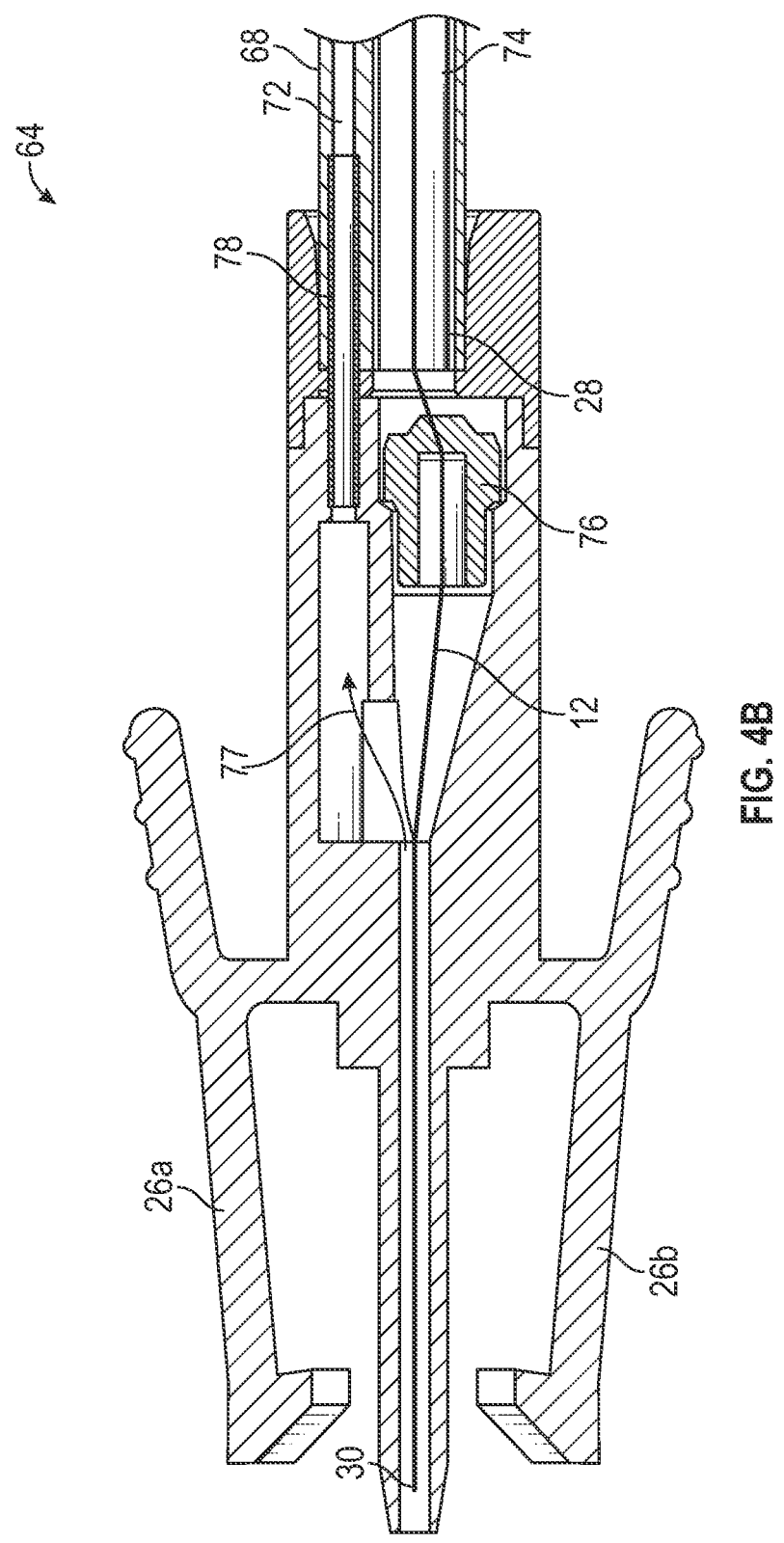
FIG. 4B is a cross-sectional top view of an example distal end of the other vascular access device, according to some embodiments.
Figure 4C:
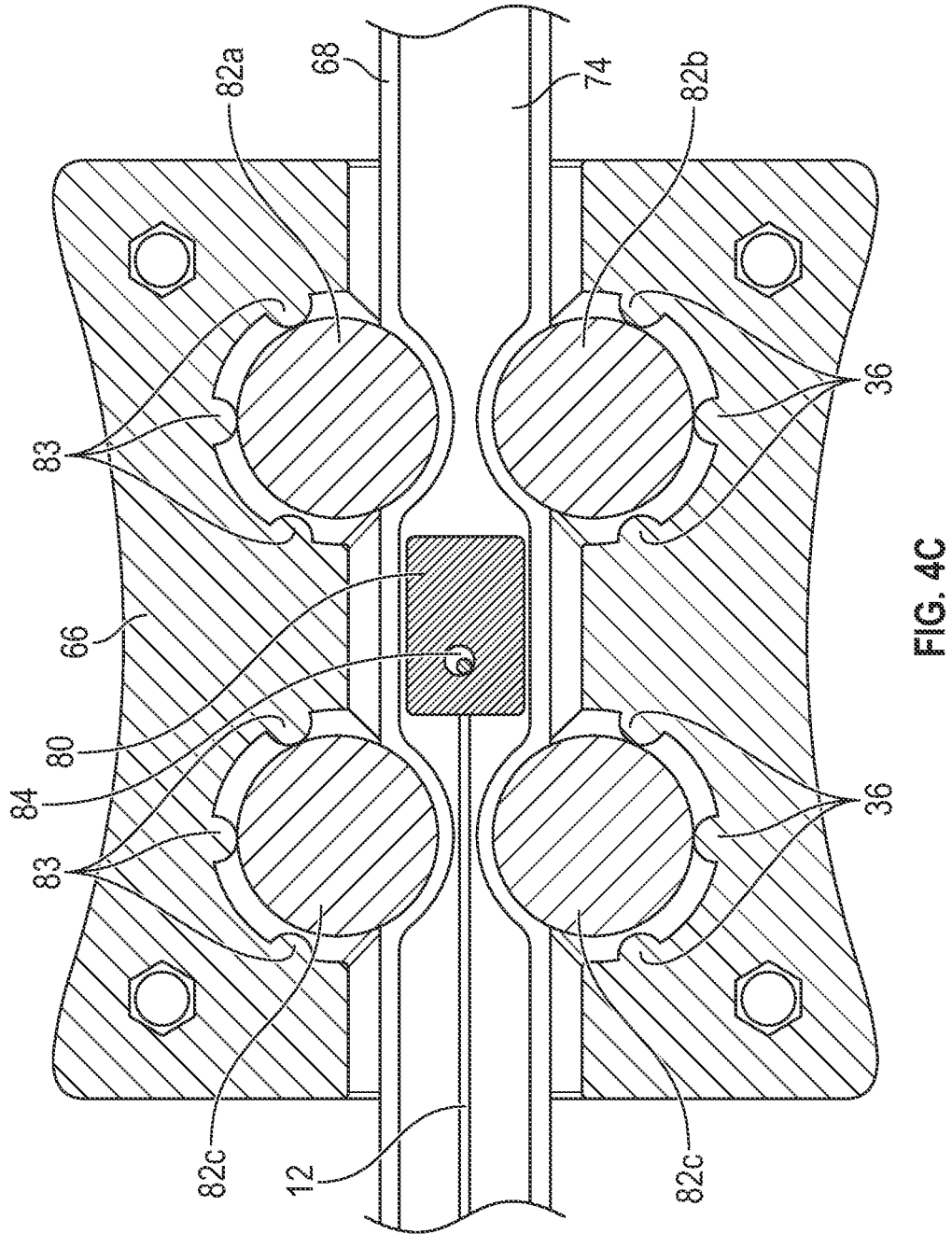
FIG. 4C is a cross-sectional view of example advancement element of the other vascular access device, illustrating an example extension tube therethrough, according to some embodiments.
Figures 4D, 4E:
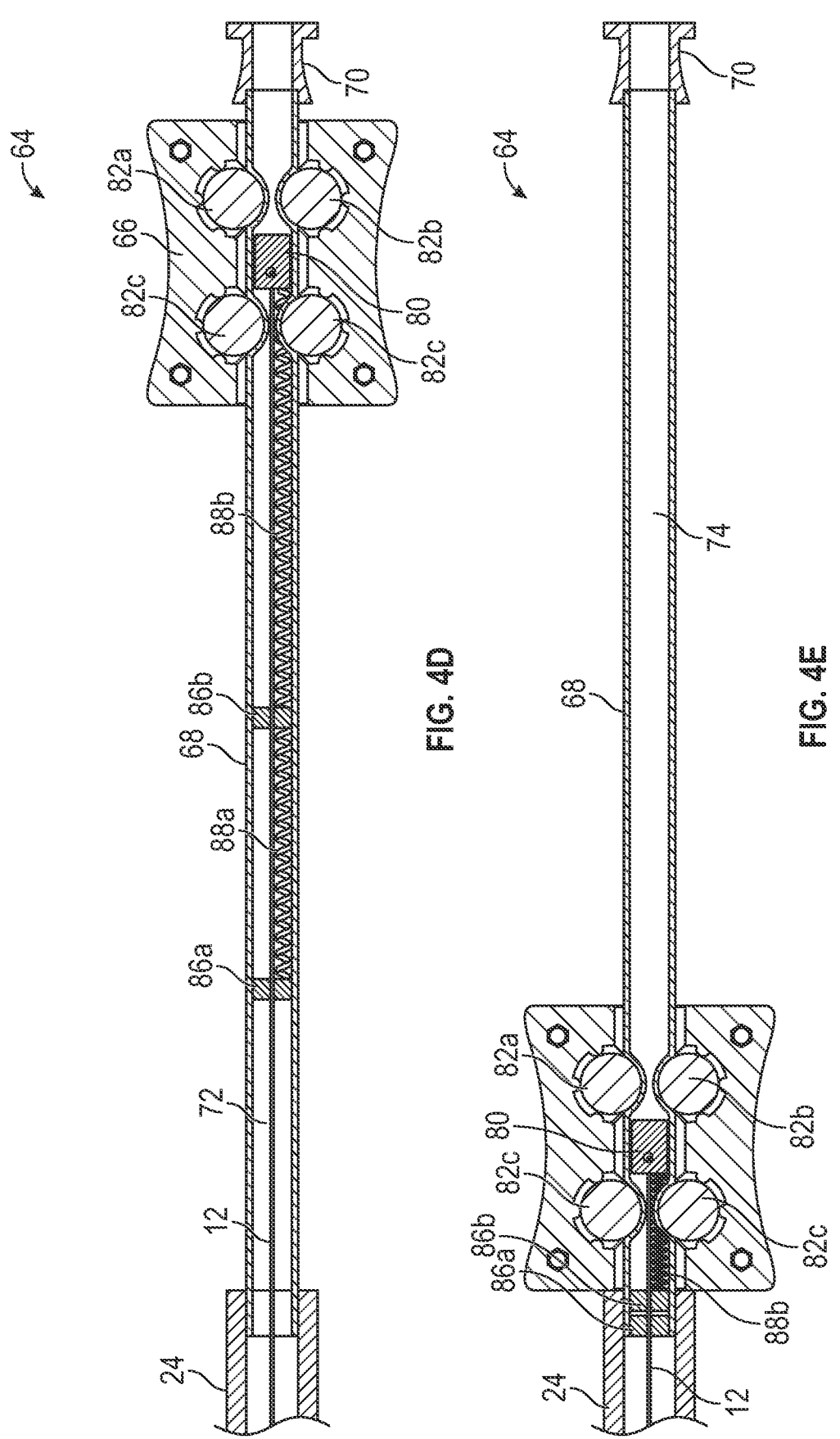
FIG. 4D is a cross-sectional view of the other vascular access device, illustrating the advancement device of the other vascular access device in an example retracted position, according to some embodiments.
FIG. 4E is a cross-sectional view of the other vascular access device, illustrating the advancement device of the other vascular access device in an example advanced position, according to some embodiments.
Figure 4F:
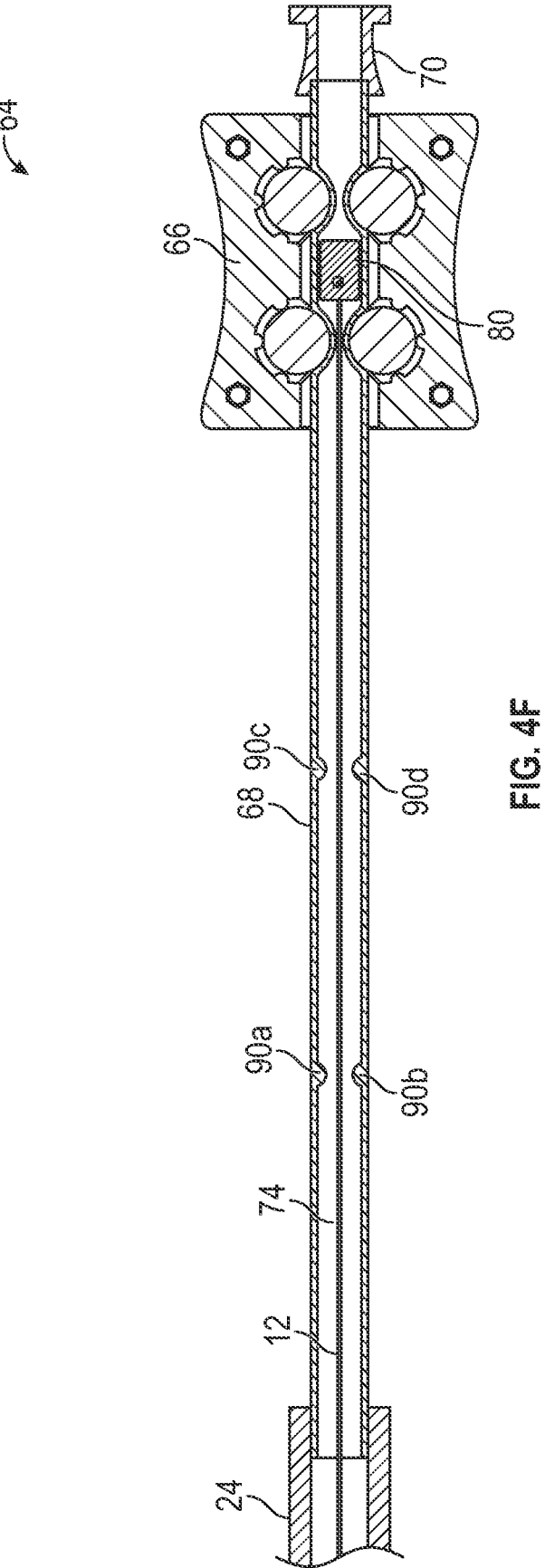
Figure 5A:
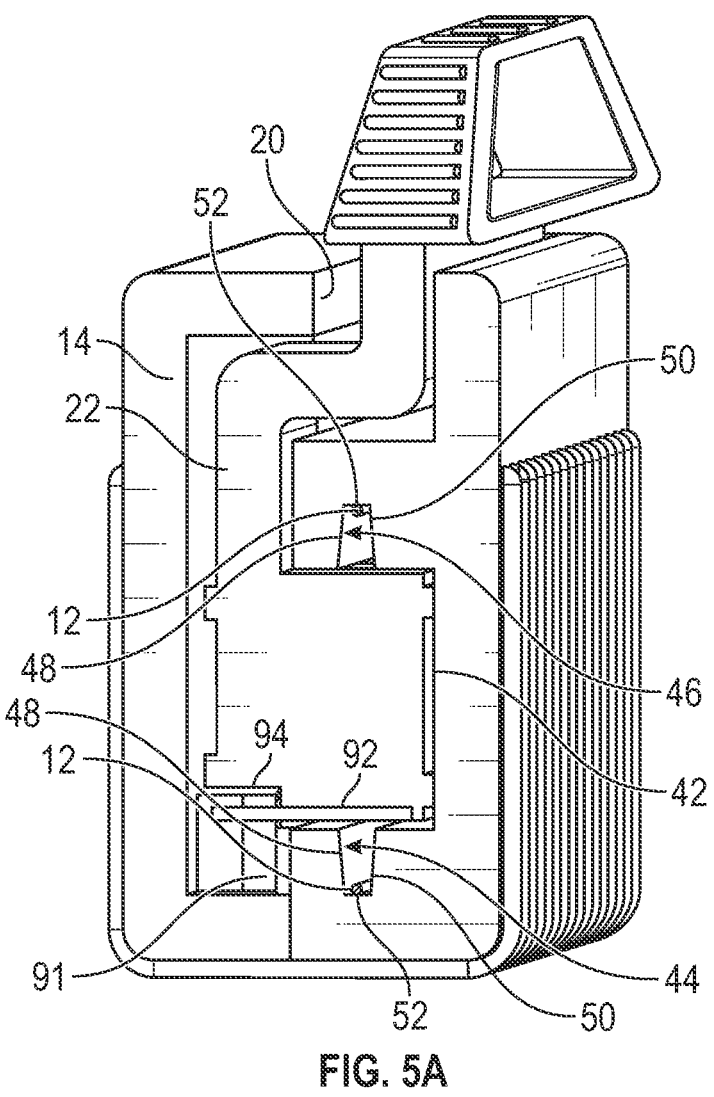
Figure 5B:
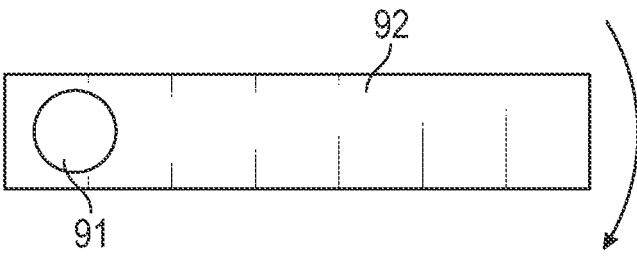
Figure 6:
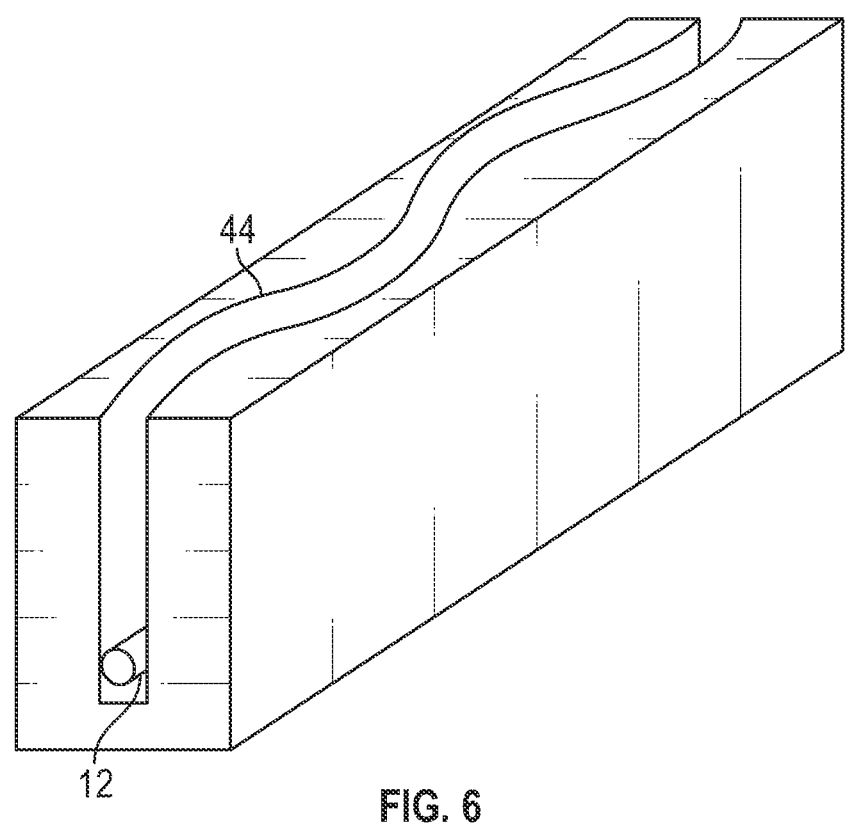
Figure 7:
Figure 8:

FIG. 4F is a cross-sectional view of the other vascular access device, illustrating example supports, according to some embodiments;

FIG. 5A is a cross-sectional view of the vascular access device along the line 1E-1E, illustrating an example motion restrictor, according to some embodiments;

FIG. 5B is a top view of the motion restrictor rotatable on an example post, according to some embodiments;

FIG. 6 is an upper perspective view of an example groove that is serpentine, according to some embodiments;

FIG. 7 is a cross-sectional view of the vascular access device, illustrating an example first probe enclosure and an example second probe enclosure protrusion, according to some embodiments; and FIG. 8 is a cross-sectional view of the vascular access device, illustrating an example first rotatable probe enclosure and an example second rotatable probe enclosure protrusion, according to some embodiments.

DETAILED DESCRIPTION

Referring now to FIGS. 1A-1E, in some embodiments, a vascular access device 10 may be configured to deliver a probe 12 through a catheter of a catheter assembly. In some embodiments, the probe 12 may be advanced through the catheter to push past any occlusions in the catheter or vasculature (e.g., thrombus or fibrin sheath at a tip of the catheter, vein collapse, valves, etc.) to create a clear pathway for fluid flow. In some embodiments, the probe 12 may reduce or remove occlusions, improving patency of the catheter for medication and fluid delivery, as well as blood acquisition, during a dwell time of the catheter.

In some embodiments, the probe 12 may include a guidewire or a tube. Additionally or alternatively, the probe 12 may include one or more sensors. In some embodiments, the sensors may be used for patient or device monitoring and may include sensors measuring pressure, temperature, pH, blood chemistry, oxygen saturation, flow rate, or another physiological property. In some embodiments, the catheter may include a peripheral intravenous (IV) catheter, a peripherally-inserted central catheter, or a midline catheter. In some embodiments, the catheter through which the probe 12 may be delivered may have been previously inserted into vasculature of a patient and may be dwelling within the vasculature when the probe 12 is advanced through the catheter.

In some embodiments, the probe 12 may be disposed within a housing 14, which may be configured to protect the probe 12 from damage and/or contamination from a surrounding external environment. In some embodiments, the housing 14 may be rigid or semi-rigid. In some embodiments, the housing 14 may be made of one or more of stainless steel, aluminum, polycarbonate, metal, ceramic, plastic, and another suitable material. In some embodiments, the housing 14 may include a proximal end 16, a distal end 18, and a slot 20. In some embodiments, the slot 20 may extend parallel to a longitudinal axis of the housing 14.

Figure 1A:
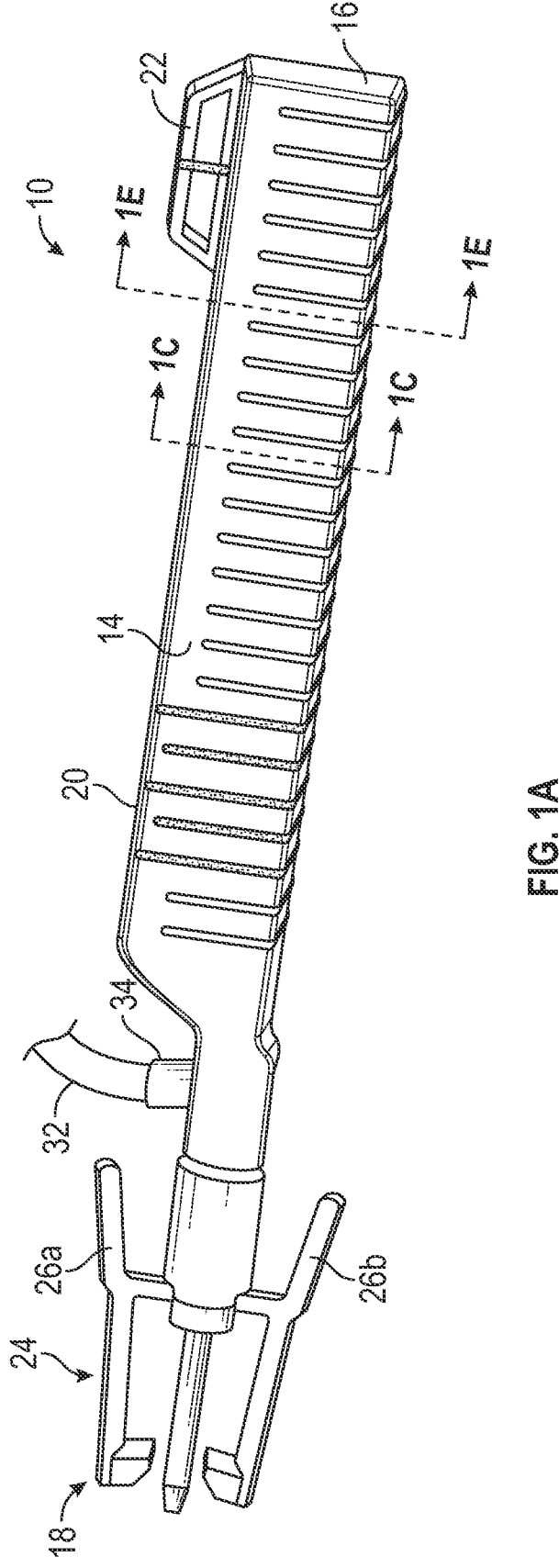
FIG. 1A is an upper perspective view of an example vascular access device, according to some embodiments.

In some embodiments, the vascular access device 10 may include an advancement element 22, which may extend through the slot 20 and may be configured to move linearly along the slot 20 between a retracted position illustrated, for example, in FIG. 1A, and an advanced position. In some embodiments, the retracted position may correspond to a fully retracted position in which the advancement element is at a proximal end of the slot 20. In some embodiments, the advanced position may correspond to a fully advanced position in which the advancement element is at a distal end of the slot 20. In some embodiments, the clinician may pinch or grasp the advancement element 22 to move the advancement element 22 between the retracted position and the advanced position.

In some embodiments, the distal end 18 of the housing 14 may include a connector 24. In some embodiments, the connector 24 may include opposing lever arms 26a, 26b. In some embodiments, distal ends of the opposing lever arms 26a, 26b may be configured to move apart from each other in response to pressure applied to proximal ends of the opposing lever arms 26a, 26b. In some embodiments, in response to removal of the pressure applied to the proximal ends of the opposing lever arms 26a, 26b, the distal ends may move closer to each other and clasp a portion of the catheter assembly, such as a needleless connector, another connector, or a proximal end of a catheter adapter, for example. In some embodiments, the connector 24 may include a blunt cannula or male luer configured to insert into the portion of the catheter assembly.

In some embodiments, the connector 24 may include any suitable connector. For example, the connector 24 may include a threaded male luer, a slip male luer, a threaded male luer with a spin lock, a threaded male luer with a removable blunt cannula snap connection, a slip male luer with a removable blunt cannula snap connection, or another suitable connector. In some embodiments, the connector 24 may include one or more bond pockets, which may each be configured to receive an extension tube. In some embodiments, the connector 24 may be monolithically formed as a single unit with a body of the housing 14 that includes the slot 20.

In some embodiments, the probe 12 may include a first end 28 and a second end 30. In some embodiments, movement of the advancement element 22 from the retracted position to the advanced position may cause the second end 30 of the probe 12 to be advanced beyond the distal end 18 of the housing 14. In some embodiments, moving the advancement element 22 to the advanced position may introduce the probe 12 into the catheter assembly and/or through the catheter. In some embodiments, in response to the probe 12 being introduced into the catheter assembly and/or through the catheter, the probe 12 may access a fluid pathway of the catheter assembly and/or the vasculature of the patient.

In some embodiments, the catheter of the catheter assembly with significant dwelling time within the vasculature may be susceptible to narrowing, collapse, kinking, blockage by debris (e.g., fibrin or platelet clots), and adhering of a tip of the catheter to the vasculature. Thus, blood withdrawal using the catheter may be difficult. In some embodiments, the probe 12 may have a diameter less than a diameter of the catheter of the catheter assembly to provide access to the vasculature of the patient without any additional needle sticks. In some embodiments, the probe 12 may clear the pathway for collecting a blood sample. Thus, in some embodiments, the vascular access device 10 may be used for needle-free blood collection and/or fluid infusion.

In some embodiments, an extension tube 32 may be coupled to the vascular access device 10, and the extension tube 32 may be used for blood collection and/or fluid infusion. In some embodiments, the extension tube 32 may extend from a port 34 of the housing 14. In some embodiments, a fluid seal 36 may be within the housing 14 to enable the probe 12 to advance and/or retract while maintaining a closed fluid path. In some embodiments, the probe 12 may be configured to extend through the fluid seal 36, which may include a septum. In some embodiments, the fluid seal 36 may be disposed proximal to the port 34 and distal to the advancement element 22 in the advanced position. In some embodiments, the fluid seal 36 may include silicone, rubber, an elastomer, or another suitable material. In some embodiments, the fluid seal 36 may include an aperture, slit, or the like to accommodate the probe 12 therethrough.

In some embodiments, a proximal end of the extension tube 32 may be coupled to a blood collection device 38. For example, the proximal end of the extension tube 32 may be integrated with a connector 40, which may be coupled to the blood collection device 38. In some embodiments, a needle-less connector may be disposed between the connector 40 and the blood collection device 38. In some embodiments, the blood collection device 38 may include a syringe, a BD VACUTAINER® one-use holder (available from Becton, Dickinson and Company of Franklin Lakes, New Jersey), a BD VACUTAINER® LUER-LOK™ access device (also available from Becton, Dickinson and Company of Franklin Lakes, New Jersey), or another suitable blood collection device, which may provide suction. In some embodiments, the connector 40 and/or the port 34 may be coupled to an IV line or another fluidic connection.

In some embodiments, an inner surface 42 of the housing 14 may include one or more grooves. For example, the inner surface 42 may include a first groove 44 and/or a second groove 46. In some embodiments, the first groove 44 and/or the second groove 46 may be disposed within the housing 14 between the proximal end 16 and the distal end 18. In some embodiments, the probe 12 may be disposed within the first groove 44 and/or the second groove 46. In some embodiments, the first groove 44 and/or the second groove 46 may include a support wall 48, another support wall 50 opposite the support wall, and a bottom 52 extending between the support wall 48 and the other support wall 50. In some embodiments, the first groove 44 and/or the second groove 46 may be open opposite the bottom 52. In some embodiments, the first groove 44 and/or the second groove 46 may be linear and/or configured to guide the probe 12 as the probe 12 is advanced distally and/or retracted proximally.

In some embodiments, the advancement element 22 may include an arc-shaped channel 54, which may be U-shaped. In some embodiments, the probe 12 may extend and move through the arc-shaped channel 54. In some embodiments, the first end 28 of the probe 12 may be fixed. In some embodiments, the first end 28 of the probe may be fixed within the housing 14. In some embodiments, in response to movement of the advancement element 22 a first distance, the second end of the probe 12 may be configured to advance distally a second distance. In some embodiments, the second distance may be twice the first distance. In these embodiments, the advancement element 22 and the probe 12 may have a 1:2 advancement ratio such that for a particular distance the advancement element 22 is moved along the slot 20, the second end 28 of the probe 12 is moved twice the particular distance. In some embodiments, the second distance may be more than twice the first distance. In these and other embodiments, the probe 12 may extend through multiple U-shapes or other arc-shapes.

It is understood that in some embodiments, the vascular access device 10 may not include the arc-shaped channel 54, and the first end 28 of the probe 12 may be attached to the advancement element 22. In these embodiments, the advancement element 22 and the probe 12 have a 1:1 advancement ratio such that for a particular distance the advancement element 22 is moved along the slot 20, the second end 28 of the probe 12 is moved the particular distance or a same amount.

Figure 1B:
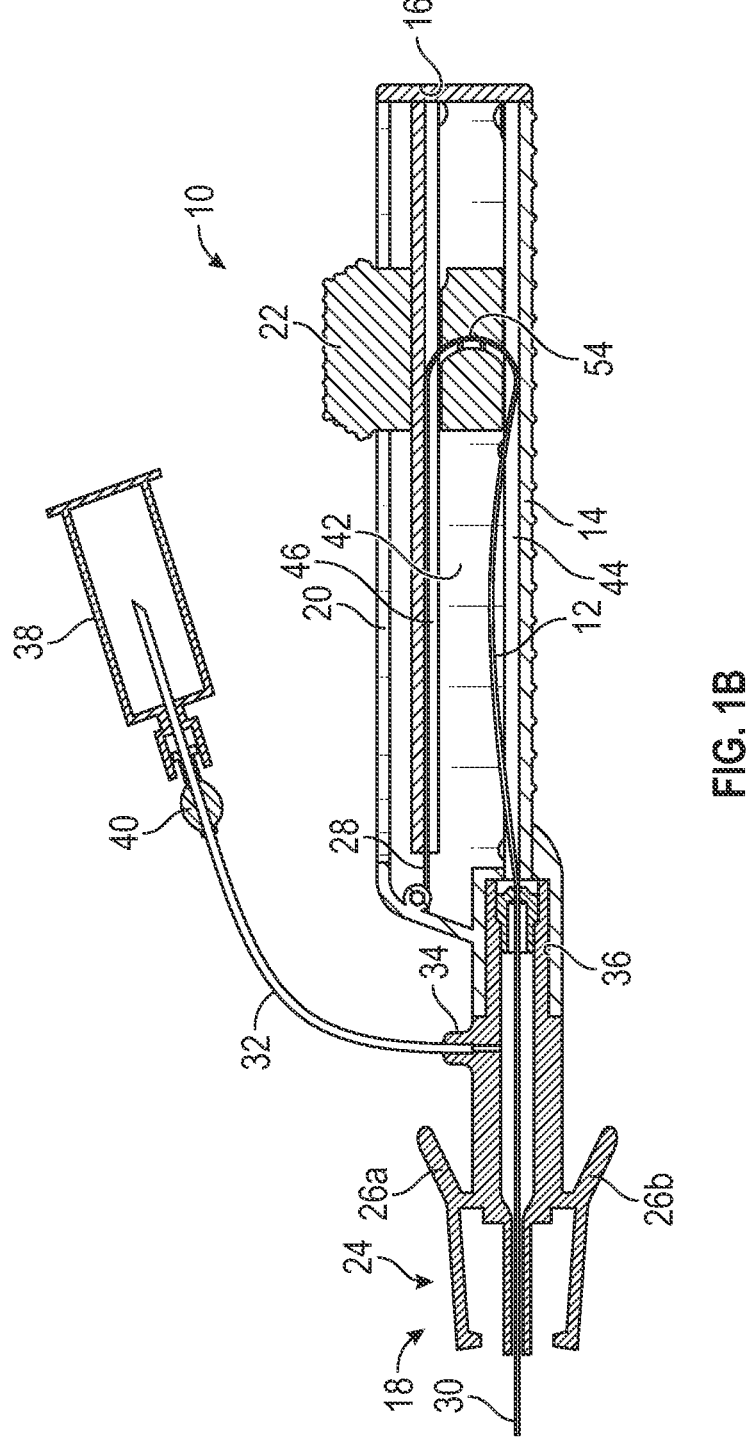
FIG. 1B is a cross-sectional view of the vascular access device.
Figure 1C:
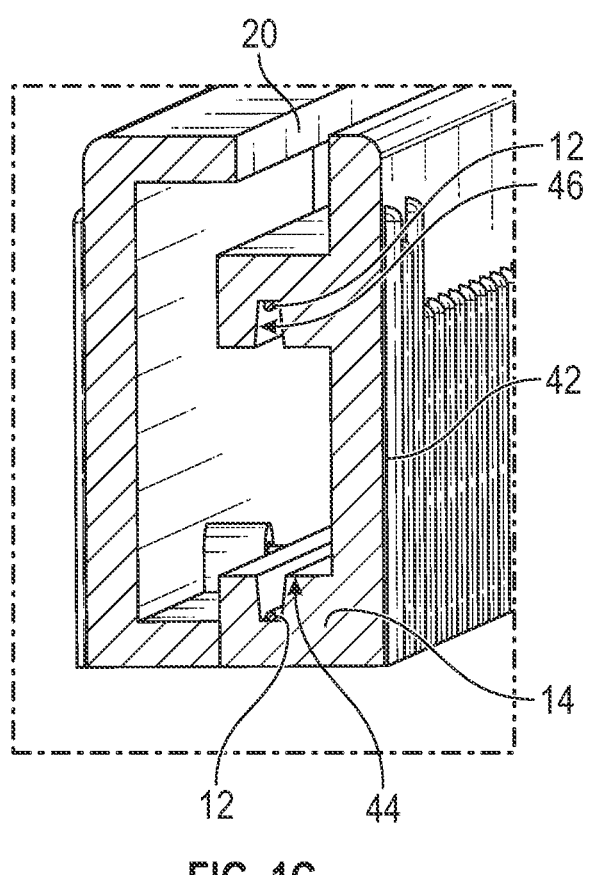
FIG. 1C is a cross-sectional view of the vascular access device along the line 1C-1C of FIG. 1A, according to some embodiments.
Figure 1D:
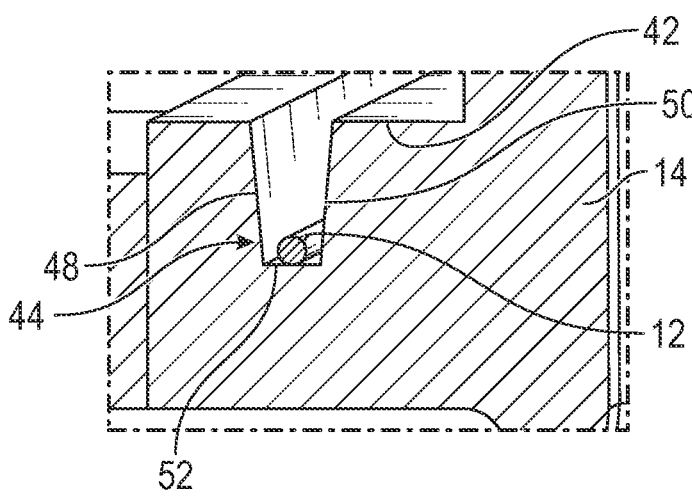
FIG. 1D is an enlarged view of a portion of FIG. 1C, according to some embodiments.
Figure 1E:
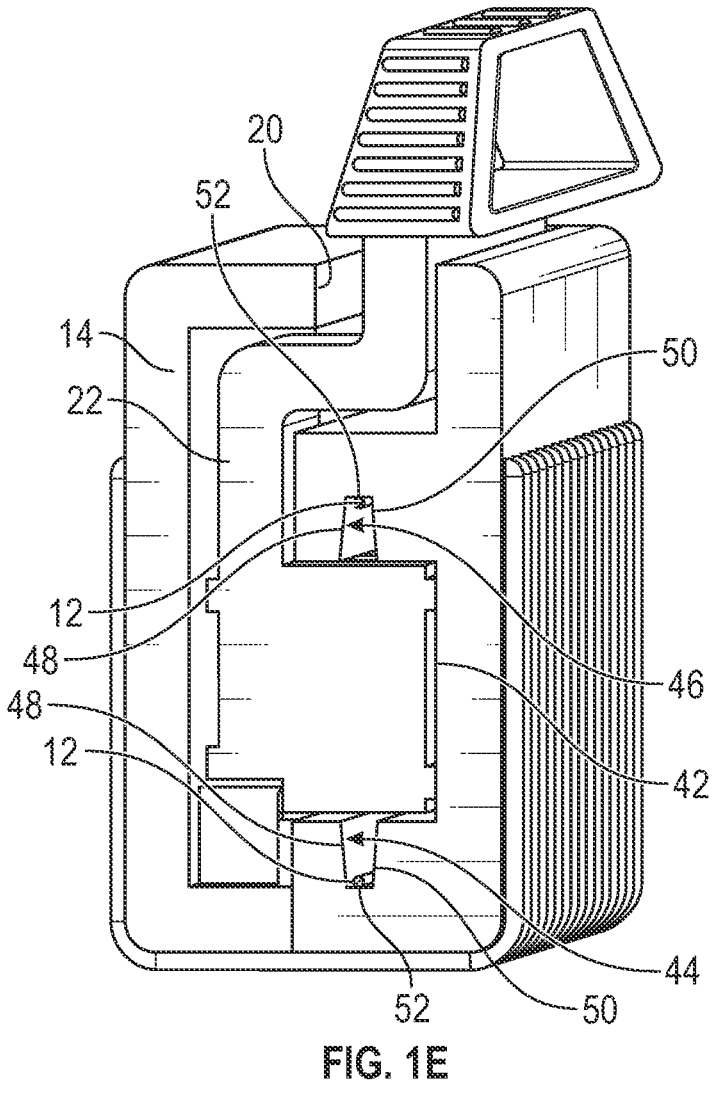
FIG. 1E is a cross-sectional view of the vascular access device along the line 1E-1E, according to some embodiments.

In some embodiments, because the first groove 44 and/or the second groove 46 are open opposite the bottom 52, the probe 12 may tend to buckle in response to the advancement element 22 being advanced distally, as illustrated, for example, in FIG. 1B. In some embodiments, the vascular access device 10 may be configured to reduce buckling of the probe 12 through various features described in FIGS. 2-8.

Figure 2A:
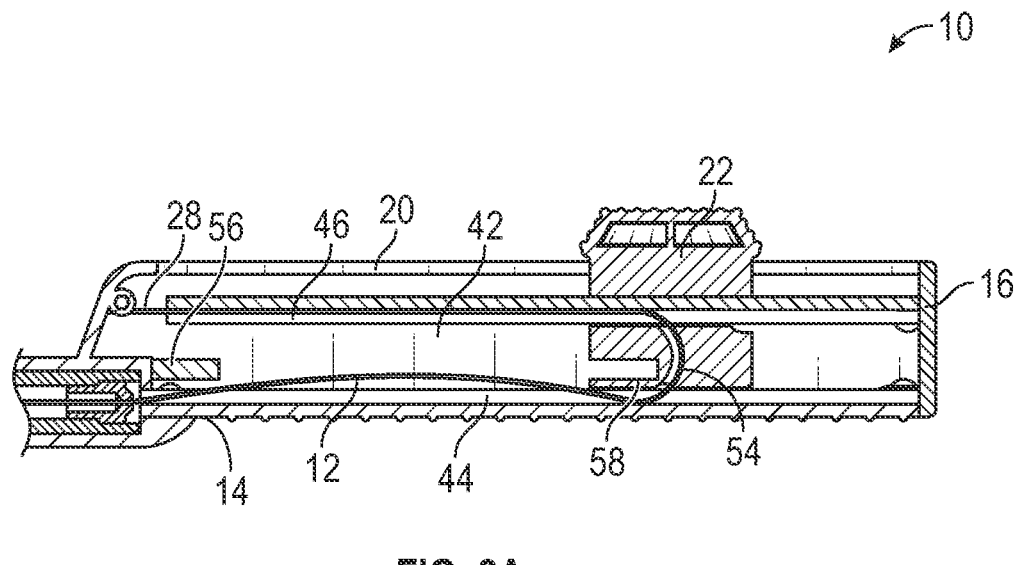
FIG. 2A is a cross-sectional view of the vascular access device, illustrating an example protrusion and an example recess, according to some embodiments.
Figure 2B:
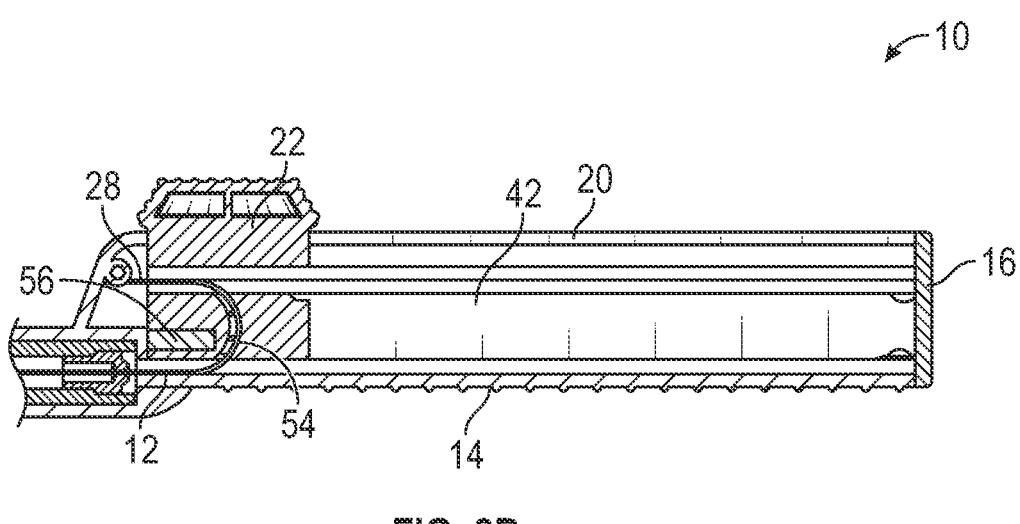
FIG. 2B is a cross-sectional view of the vascular access device, illustrating an example protrusion, an example recess, and an example advancement element in an example advanced position, according to some embodiments.

Referring now to FIGS. 2A-2B, in some embodiments, the vascular access device 10 may include a protrusion 56 fixed within the housing 14. In some embodiments, the protrusion 56 may be distal to the advancement element 22 when the advancement element 22 is in the retracted position. In some embodiments, the protrusion 56 may extend from the inner surface 42 of the housing 14 and/or may be monolithically formed with the housing 14 as a single unit. In some embodiments, the protrusion 56 may be disposed within the distal end 18 of the housing 14. In some embodiments, the probe 13 may be disposed between the protrusion 56 and the inner surface 27 of the housing 14.

In some embodiments, a length of the protrusion 56 from a distal end of the protrusion 56 to a proximal end of the protrusion 56 may be less than a length from a distal end of the advancement element 22 to the arc-shaped channel 54. In some embodiments, a distal end of the advancement element 22 may include a recess 58 configured to receive the protrusion 56 when the advancement element 22 is in the advanced position.

In some embodiments, the protrusion 56 may be elongated in a distal-proximal direction. In some embodiments, the recess 58 may be elongated and/or sized to fit the protrusion 56, which may include a corresponding shape to the recess 58 to support the protrusion 56. In some embodiments, the protrusion 56 may include a rectangular cuboid or another suitable shape configured to limit buckling of the probe 13. In some embodiments, a bottom surface of the protrusion 56 facing towards the first groove 44 may be configured to contact the probe 13 during advancement of the advancement element 22 and the probe 13 in a distal direction, which may reduce buckling of the probe 13.

Figure 3A:
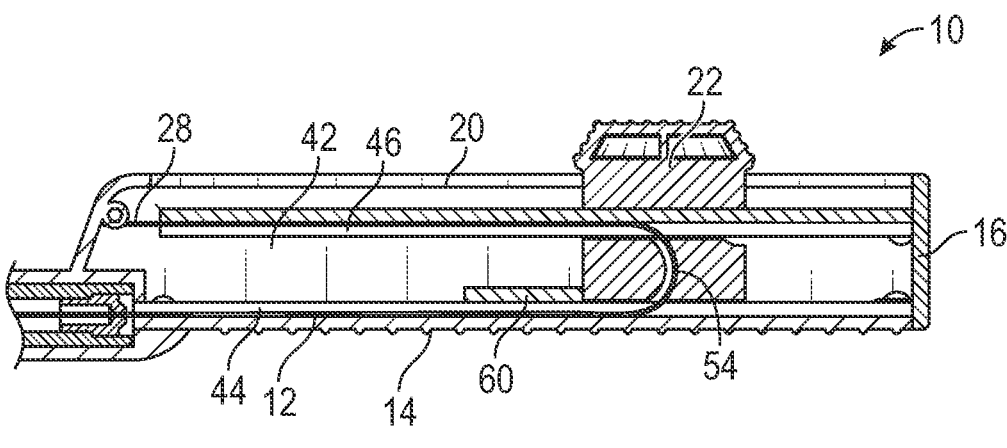
FIG. 3A is a cross-sectional view of the vascular access device, illustrating an example distally-extending arm, according to some embodiments.
Figure 3B:
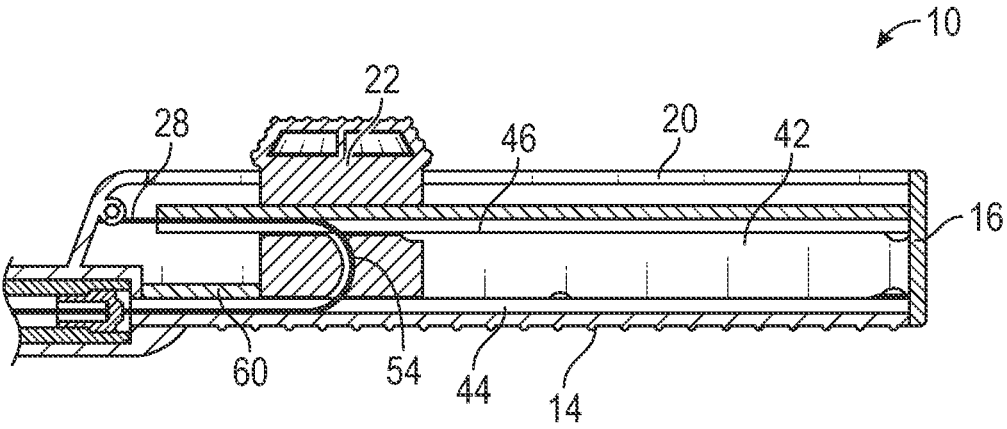
FIG. 3B is a cross-sectional view of the vascular access device, illustrating the distally-extending arm and the advancement element in an example advanced position, according to some embodiments.

Referring now to FIGS. 3A-3B, in some embodiments, the advancement element 22 may include a distally-extending arm 60. In some embodiments, the probe 13 may be disposed between the distally-extending arm 60 and the inner surface 27 of the housing 14. In some embodiments, a bottom surface of the distally-extending arm 60 facing towards the first groove 44 may be configured to contact the probe 13 during advancement of the advancement element 22 and the probe 13 in a distal direction, which may reduce buckling of the probe 13. In some embodiments, the distally-extending arm 60 may include a rectangular cuboid or another suitable shape configured to limit buckling of the probe 13. In some embodiments, the distally-extending arm 60 may contact the support wall 48 and/or the other support wall 50 (see, for example, FIGS. 1C-1E) to keep the probe 12 within the first groove 44.

Figure 3C:
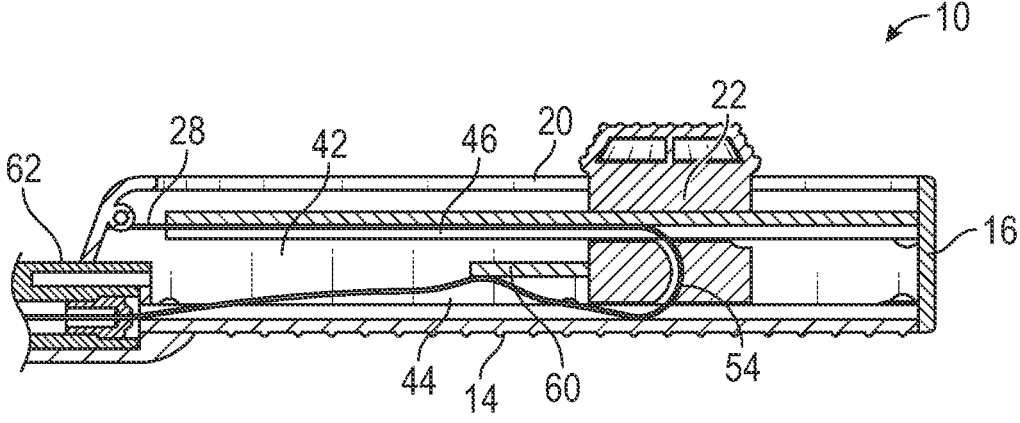
FIG. 3C is a cross-sectional view of the vascular access device, illustrating an example distally-extending arm and an example recess, according to some embodiments.

Referring now to FIG. 3C, in some embodiments, the housing 14 may include a recess 62 configured to receive the distally-extending arm 60 when the advancement element 22 is in the advanced position. In some embodiments, the recess 62 may be disposed within the distal end 18 of the housing 14. In some embodiments, the recess 62 may be monolithically formed as a single unit with the housing 14. In some embodiments, the recess 62 may be elongated and/or sized to fit the distally-extending arm 60, which may include a corresponding shape to the recess 62 to support the distally-extending arm 60. In some embodiments, the distally-extending arm 60 may contact the support wall 48 and/or the other support wall 50 (see, for example, FIGS. 1C-1E) to keep the probe 12 within the first groove 44, and the recess 62 may be positioned in alignment with a top of the support wall 49 and/or the other support wall 50.

Referring now to FIGS. 4A-4C, another vascular access device 64 is illustrated, according to some embodiments. In some embodiments, the vascular access device 64 may be similar or identical to the vascular access device 10 in terms of one or more features and/or operation. In some embodiments, the vascular access device 64 may include an advancement element 66 and an extension tube 68 extending through the advancement element 66. In some embodiments, the extension tube 68 may include a coextruded guidewire to add stiffness to the extension tube 68. In some embodiments, the extension tube 68 may include a multi-lumen extension tube.

In some embodiments, the vascular access device 64 may include the probe 12, which may include a guidewire, a tube, or another suitable instrument. In some embodiments, the probe 12 may be colored to increase visibility. In some embodiments, the probe 12 may be the guidewire, and the guidewire may be constructed of metal or another suitable material. In these and other embodiments, the probe 12 may be lubricated or coated to ease advancement.

In some embodiments, the probe 12 may include a guidewire, which may include a spring or coil. In some embodiments, the spring or coil may include varying pitches along a length of the spring or coil. For example, a pitch of the spring or coil upstream from or proximal to a catheter tip may be larger to facilitate more blood flow and increase flow rate, and a pitch of the spring or coil near the catheter tip may be smaller to prevent blood clots from entering the catheter tip, while still allowing blood to flow through it. In some embodiments, the guidewire may include a rod, which may extend through a center portion of the spring or coil. In some embodiments, the guidewire may include the rod and may not include the spring or coil.

As mentioned, over time a catheter can become occluded due to presence of fibrin sheath, thrombus, or vein walls or valves. In some embodiments, the probe 12 may be configured to extend into and/or through the catheter assembly to push through and/or disrupt an occlusion of the catheter. In some embodiments, the probe 12 may overcome thrombus and fibrin sheath in or around the catheter assembly or in the vein that might otherwise prevent blood draw. In some embodiments, the vascular access device 64 may reduce trauma to the vasculature while also facilitating fluid delivery, blood collection, patient or device monitoring, or other clinical needs. In some embodiments, the vascular access device 64 may decrease hemolysis and reduce blood exposure.

In some embodiments, a distal end of the vascular access device 64 may include the connector 24 or another suitable connector. In some embodiments, the connector 24 may be configured to couple to the catheter assembly, which may be existing or already dwelling within the vasculature of the patient. In some embodiments, the catheter assembly may include a catheter adapter, which may include a distal end, a proximal end, and a lumen extending through the distal end of the catheter adapter and the proximal end of the catheter adapter. In some embodiments, the catheter may extend from the distal end of the catheter adapter. In some embodiments, the catheter may include a peripheral intravenous catheter, a midline catheter, or a peripherally inserted central catheter. In some embodiments, the catheter assembly may include an introducer needle, which may extend through the catheter and facilitate piercing of skin and the vasculature to insert the catheter into the patient. In some embodiments, the introducer needle may be removed from the catheter assembly prior to coupling of the vascular access device 64 to the catheter assembly.

In some embodiments, the catheter assembly may be straight. In other embodiments, the catheter assembly may be integrated, having an extension tube that is integrated with the catheter adapter. In some embodiments, the catheter assembly may include an extension set, which may include the extension tube extending from and integrated with a side port of the catheter adapter. In some embodiments, the connector 24 may be configured to couple to a portion of the catheter assembly, such as the proximal end of the catheter adapter and/or a needleless access connector. In some embodiments, the needleless access connector may be coupled to a proximal end, a T-connector, or another portion of the extension set. In some embodiments, the needleless access connector may be permanently connected, such as, for example, via adhesive, to the connector 24 to prevent intentional or unintentional removal by a user.

In some embodiments, a distal end of the extension tube 68 may be coupled to the connector 24. In some embodiments, a proximal end of the extension tube 68 may be coupled to another connector 70, which may be configured to couple to a blood collection device, such as, for example the blood collection device 38 discussed with respect to FIG. 1.

In some embodiments, the probe 12 may be advanced prior to or during infusion or blood draw. In some embodiments, after completing a blood draw or infusion and before uncoupling the vascular access device 64 from the catheter assembly, the user may retract the probe 12 by moving the advancement element 66 backward or proximally. Thus, in some embodiments, a risk of exposure of the user to blood may be decreased.

As illustrated in FIG. 4B, in some embodiments, the extension tube 68 may include a first lumen 72 and a second lumen 74, which may be separate from the first lumen 72 along an entire length of the extension tube 68. In some embodiments, a blood collection pathway may extend through the first lumen 72. In some embodiments, the probe 12 may be disposed within the second lumen 74. In some embodiments, a diameter of the second lumen 74 may be larger than a diameter of the first lumen 72. In some embodiments, the diameter and/or a length of the first lumen 72 may be selected based on a desired flow rate and/or to reduce hemolysis.

In some embodiments, in response to moving the advancement element 66 distally along the extension tube 68, the probe 12 may be advanced distally within the second lumen 74. In some embodiments, in response to moving the advancement element 66 proximally along the extension tube 68, the probe 12 may be retracted proximally within the second lumen 74.

In some embodiments, the vascular access device 64 may include a septum 76 disposed within the connector 24 and configured to seal the second lumen 74 or prevent blood flow into the second lumen 74. In these and other embodiments, the septum 76 may not seal the first lumen 72 such that blood may flow proximally along a fluid pathway 77 from the connector 24 through the first lumen 72 for blood collection. In some embodiments, the septum 76 may be elastomeric.

In some embodiments, a distal end of the probe 12 may be disposed proximal to a distal end of the connector 24 when the advancement element 66 is fully retracted in a proximal direction. In some embodiments, the distal end of the probe 12 may be disposed proximal to the septum 76 when the advancement element 66 is fully retracted in the proximal direction and/or the probe 12 may be sealed within the extension tube 68.

In some embodiments, the vascular access device 64 may include a cannula 78, which may connect a distal end of the first lumen 72 and the connector 24. In some embodiments, the cannula 78 may be blunt. In some embodiments, the fluid pathway 77 may extend through the cannula 78, which may prevent blood leakage. In some embodiments, the cannula 78 may be constructed of steel, plastic, metal, or another suitable material. In some embodiments, the cannula 78 may be coupled to the connector 24 or monolithically formed with the connector 24 as a single unit. In some embodiments, the septum 76 may be concentric with the second lumen 74 or offset slightly to obtain adequate wall thicknesses.

In some embodiments, the septum 76 may extend across an entire width of an inner lumen of the connector 24. In these embodiments, the septum 76 may seal the second lumen 74 or prevent blood flow into the second lumen 74. In these embodiments, the cannula 78 may extend from the first lumen 72 through the septum 76 to allow fluid flow therethrough.

As illustrated in FIG. 4C, in some embodiments, the vascular access device 64 may include a wedge 80 disposed within the advancement element 66 and the second lumen 74 of the extension tube 68. In some embodiments, the vascular access device 64 may include a pair of opposing pinch members 82*a, b* configured to pinch the extension tube 68. In some embodiments, the pair of opposing pinch members 82*a, b* may be disposed within the advancement element 66 proximal to the wedge 80 and configured to move along the extension tube 68 with the advancement element 66.

In some embodiments, the probe 12 may extend distally from the wedge 80. In some embodiments, the probe 12 may be disposed within the second lumen 74. In some embodiments, in response to moving the advancement element 66 distally along the extension tube 68, the pair of opposing pinch members 82*a, b* may push the wedge 80 distally, and the probe 12 may be advanced distally.

In some embodiments, the vascular access device 64 may include another pair of opposing pinch members 82*c, d* configured to pinch the extension tube 68. In some embodiments, the other pair of opposing pinch members 82*c, d* may be disposed within the housing distal to the wedge 80 and configured to move along the extension tube 68 with the advancement element 66. In some embodiments, in response to moving the advancement element 66 proximally along the extension tube 68, the other pair of opposing pinch members 82*c, d* may push the wedge 80 proximally and the probe 12 may be retracted proximally.

The pair of opposing pinch members 82*a, b* and the other pair of opposing pinch members 82*c, d* may be referred to collectively in the present disclosure as "opposing pinch members 82." In some embodiments, in response to movement of the advancement element 66 along the extension tube 68, the opposing pinch members 82 may rotate with respect to the advancement element 66 and the extension tube 68. In some embodiments, in response to movement of the advancement element 66 along the extension tube 68, the opposing pinch members 82 may rotate with respect to the advancement element 66 and the extension tube 68. In some embodiments, an inner surface of the advancement element 66 may include one or more bumps 83 in contact with the opposing pinch members 82, which may reduce friction as the opposing pinch members 82 rotate. In some embodiments, the wedge 80 and/or the opposing pinch members 82 may be lubricated with a lubricant, which may reduce friction.

In some embodiments, the opposing pinch members 82 may be constructed of plastic, metal, or another suitable material. In some embodiments, the opposing pinch members 82 may include spherical balls, ball bearings, wheels, or cylinders, which may be configured to rotate with respect to the advancement element 66. In some embodiments, the opposing pinch members 82 may include the wheels, which may be smooth or include feet along their edges. In these embodiments, lubricant may be applied to axles of the wheels to reduce friction. In some embodiments, the opposing pinch members 82 may be fixed with respect to the advancement element 66. For example, the opposing pinch members 82 may be molded into the advancement element 66.

In some embodiments, a number of the opposing pinch members 82 may vary based on a shape of the wedge 80. In some embodiments, the vascular access device 64 may include the pair of opposing pinch members 82*a, b* and the other pair of opposing pinch members 82*c, d* in response to the shape of the wedge 80 being cylindrical, for example. In some embodiments, the vascular access device 64 may include a single pair of the opposing pinch members 82, such as the pair of the opposing pinch members 82*a, b*, in response to the wedge 80 including a dog bone shape, and the single pair may be disposed in a middle or depression of the dog bone shape.

In some embodiments, the wedge 80 may include an arc-shaped channel 84, which may be U-shaped. In some embodiments, the probe 12 may extend and move through the arc-shaped channel 84. In some embodiments, the first end 28 of the probe 12 may be fixed. In some embodiments, the first end 28 of the probe may be fixed within the housing 14. In some embodiments, in response to movement of the advancement element 66 a first distance, the second end of the probe 12 may be configured to advance distally a second distance. In some embodiments, the second distance may be twice the first distance. In some embodiments, the second distance may be more than twice the first distance. In these and other embodiments, the probe 12 may extend through multiple U-shapes or other arc-shapes.

Referring now to FIGS. 4D-4E, in some embodiments, the vascular access device 64 may include one or more supports 86 disposed within the second lumen 74 distal to the wedge 80 and configured to contact and support the probe 12. In some embodiments, in response to movement of the advancement element 66 from the retracted position to the advanced position by the user, the advancement element 66 may be configured to push the supports 86 distally. In some embodiments, the supports 86 may be constructed of an elastomer or another suitable material. In some embodiments, the supports 86 may span a particular lumen and may each have an opening therethrough configured to receive the probe 12. In some embodiments, a diameter of the opening may be approximately equal to or slightly greater than an outer diameter of the probe 12.

In some embodiments, the vascular access device 64 may include one or more tethers 88 connecting the advancement element 22 to one or more of the supports 86. In some embodiments, in response to movement of the advancement element 22 from the advanced position to the retracted position, the tethers 88 may be configured to pull the supports 86 proximally back to an initial position. In some embodiments, there may be a particular tether 88 connected to the advancement element 22 and a distalmost one of the supports 86. In these embodiments, the particular tether 88 may be the only tether and may contact any supports 86 proximal to the distalmost one of the supports 86 to pull the supports 86 proximally. In some embodiments, the vascular access device 64 may include a first tether 88a connected to a first support 86a and a second support 86b, and a second tether 88b connected to the second support 86b and the advancement element 22.

Referring now to FIG. 4F, in some embodiments, the vascular access device may include multiple supports, which may include a first protrusion 90a and a second protrusion 90b opposite the first protrusion 90a. In some embodiments, the first protrusion 90a and/or the second protrusion 90b may include a dome shape. In some embodiments, the supports may include a third protrusion 90c and a fourth protrusion 90d opposite the third protrusion 90c. In some embodiments, the third protrusion 90c and/or the fourth protrusion 90d may each include the dome shape. In some embodiments, one or more of the first protrusion 90a, the second protrusion 90b, the third protrusion 90c and the fourth protrusion 90d may be configured to contact and support the probe 12 during advancement of the probe 12 in the distal direction and/or retraction of the probe 12 in the proximal direction.

Referring now to FIGS. 5A-5B, in some embodiments, the vascular access device 10 may include a post 91, which may be coupled to the inner surface 42 of the housing 14. In some embodiments, the vascular access device 10 may include a motion restrictor 92 rotatably mounted on the post 91. In some embodiments, the motion restrictor 92 may extend over a particular groove in which the probe 12 is positioned, such as the first groove 44. In some embodiments, in response to movement of the advancement element 22 from the retracted position to the advanced position, the motion restrictor 92 may be configured to rotate on the post 91. In some embodiments, the advancement element 22 may include a cutout portion 94 configured to fit the post and the motion restrictor 92 in a rotated position and allow the advancement element 22 to move distally past the post 91 and the motion restrictor 92.

Referring now to FIG. 6, in some embodiments, a particular groove in which the probe 12 travels may be curved. For example, the first groove 44 may be curved, which may reduce buckling of the probe 12 when the probe 12 moves distally. For example, the first groove 44 may be serpentine or curve back and forth to reduce buckling of the probe 12 when the probe 12 moves distally.

Referring now to FIG. 7, in some embodiments, the vascular access device 10 may include a first probe enclosure 96 and a second probe enclosure 98. In some embodiments, the first probe enclosure 96 and the second probe enclosure 98 may be tubular. In some embodiments, the first probe enclosure 96 may include a first serpentine slot 100, and the second probe enclosure 98 may include a second serpentine slot 102. In some embodiments, the first serpentine slot 100 and the second serpentine slot 102 may each create alternating tabs, which may facilitate placement of the probe 12 within the first probe enclosure 96 and the second probe enclosure 98 and reduce buckling of the probe 12.

In some embodiments, the vascular access device 10 may include a first flexible arm 104 extending outwardly from the advancement element 22 and/or through the first serpentine slot 100 of the first probe enclosure 96. In some embodiments, the probe 12 may extend through a portion of the first flexible arm 104. In some embodiments, the portion of the first flexible arm 104 may be disposed first probe enclosure 96 and may include a hole through which the probe 12 may extend.

In some embodiments, the vascular access device 10 may include a second flexible arm 106 extending outwardly from the advancement element 22 and/or through the second serpentine slot 102 of the second probe enclosure 98. In some embodiments, the probe 12 may extend through a portion of the second flexible arm 106. In some embodiments, the portion of the second flexible arm 106 may be disposed within second probe enclosure 98 and may include a hole through which the probe 12 may extend. In some embodiments, the first flexible arm 104 may include a living hinge or a spring. Similarly, in some embodiments, the second flexible arm 106 may include a living hinge or a spring.

In some embodiments, the probe 12 may include a guidewire. In some embodiments, when the advancement tab 22 is advanced distally, the probe 12 may be pulled around the alternating tabs and the probe 12 may be advanced distally. In some embodiments, one or more of the probe 12, the first probe enclosure 96, and the second probe enclosure 98 may be lubricated with silicone or another suitable material, which may reduce drag when the probe 12 is advanced distally.

Referring now to FIG. 8, in some embodiments, the vascular access device 10 may include a first rotatable probe enclosure 108 and/or a second rotatable probe enclosure 110 configured to rotate with respect to the housing 14. In some embodiments, the first rotatable probe enclosure 108 may include a first helical slot 112, which may wind around the first rotatable probe enclosure 108. In some embodiments, the second rotatable probe enclosure 110 may include a second helical slot 114, which may wind around the second rotatable probe enclosure 110. In some embodiments, a support 115a may extend through the first helical slot 112 and a support 115b may extend through the second helical slot 114. In some embodiments, the probe 12 may extend through the support 115a and the support 115b, which may reduce kinking of the probe 12 as the first rotatable probe enclosure 108 and the second rotatable probe enclosure 110 rotate.

In some embodiments, the probe 12 may extend through the first helical slot 112 and the second helical slot 114. In some embodiments, in response to movement of the advancement element 22 along the slot 20 (see, for example, FIGS. 1A-1E), the first rotatable probe enclosure 108 and the second rotatable probe enclosure 110 may be configured to rotate or spin. In some embodiments, the first rotatable probe enclosure 108 and the second rotatable probe enclosure 110 may rotate along their respective longitudinal axes, which may be parallel to the slot 20 and a longitudinal axis of the vascular access device 10. In some embodiments, the first probe enclosure 108 and the second probe enclosure 110 may be tubular. In some embodiments, one or more bearing surfaces may be disposed within the housing 14, and the first rotatable probe enclosure 108 and the second rotatable probe enclosure 110 may be configured to rotate on the bearing surfaces.

All examples and conditional language recited herein are intended for pedagogical objects to aid the reader in understanding the invention and the concepts contributed by the inventor to furthering the art and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed is:

1. A vascular access device, comprising:
a housing, comprising a proximal end, a distal end, and a slot between the proximal end and the distal end;
a protrusion fixed within the housing distal to an advancement element;
the advancement element extending through the slot and configured to move linearly along the slot between a retracted position and an advanced position, wherein a distal end of the advancement element comprises a recess configured to receive the protrusion when the advancement element is in the advanced position; and
a probe comprising a first end and a second end, wherein the probe is disposed between the protrusion and an inner surface of the housing, wherein in response to movement of the advancement element from the retracted position to the advanced position, the second end of the probe is advanced beyond the distal end of the housing.

2. The vascular access device of claim 1, wherein the inner surface of the housing comprises a groove disposed within the housing between the proximal end of the housing and the distal end of the housing, wherein the probe is configured to move within the groove in response to the advancement element moving linearly along the slot between the retracted position and the advanced position.

3. The vascular access device of claim 2, wherein the groove is linear.

4. The vascular access device of claim 2, wherein the advancement element comprises an arc-shaped channel, wherein the probe extends through the arc-shaped channel, wherein the first end of the probe is fixed, wherein in response to movement of the advancement element a first distance, the second end of the probe is configured to advance distally a second distance, wherein the second distance is at least twice the first distance, wherein the groove is a first groove, wherein the inner surface of the housing comprises a second groove between the proximal end of the housing and the distal end of the housing and generally parallel to the first groove, wherein the probe extends through the second groove.

5. A vascular access device, comprising:
a housing, comprising a proximal end, a distal end, and a slot between the proximal end and the distal end;
an advancement element extending through the slot and configured to move linearly along the slot between a retracted position and an advanced position, wherein the advancement element comprises a distally-extending arm; and
a probe comprising a first end and a second end, wherein the probe is disposed between the distally-extending arm and an inner surface of the housing, wherein in response to movement of the advancement element from the retracted position to the advanced position, the second end of the probe is advanced beyond the distal end of the housing, wherein the housing comprises a recess configured to receive the distally-extending arm when the advancement element is in the advanced position.

6. The vascular access device of claim 5, wherein an inner surface of the housing comprises a groove disposed within the housing between the proximal end of the housing and the distal end of the housing, wherein the probe is configured to move within the groove in response to the advancement element moving linearly along the slot between the retracted position and the advanced position.

7. The vascular access device of claim 6, wherein the groove is linear.

8. The vascular access device of claim 6, wherein the advancement element comprises an arc-shaped channel, wherein the probe extends through the arc-shaped channel, wherein the first end of the probe is fixed, wherein in response to movement of the advancement element a first distance, the second end of the probe is configured to advance distally a second distance, wherein the second distance is at least twice the first distance, wherein the groove is a first groove, wherein the inner surface of the housing comprises a second groove between the proximal end of the housing and the distal end of the housing and generally parallel to the first groove, wherein the probe extends through the second groove.

* * * * *